United States Patent [19]

Riebel et al.

[11] Patent Number: 4,614,537
[45] Date of Patent: Sep. 30, 1986

[54] N-ACYL-PIPERIDONE KETAL COMPOUNDS AND THEIR USE AS ANTIDOTES FOR PROTECTING CROP PLANTS FROM HERBICIDAL DAMAGE

[75] Inventors: Hans-Jochem Riebel, Wuppertal; Ludwig Eue, Leverkusen; Wilfried Faust, Odenthal; Uwe Priesnitz, Unna-Massen, all of Fed. Rep. of Germany

[73] Assignee: Bayer Aktiengesellschaft, Leverkusen, Fed. Rep. of Germany

[21] Appl. No.: 545,472

[22] Filed: Oct. 25, 1983

Related U.S. Application Data

[60] Division of Ser. No. 425,801, Sep. 28, 1982, Pat. No. 4,548,639, which is a continuation of Ser. No. 166,280, Jul. 7, 1980, abandoned.

[30] Foreign Application Priority Data

Jul. 26, 1979 [DE] Fed. Rep. of Germany ....... 2930449

[51] Int. Cl.$^4$ .................. A01N 25/32; C07D 211/46; C07D 211/74
[52] U.S. Cl. .......................................... 71/94; 71/92; 71/100; 71/118; 71/90; 546/207; 546/242
[58] Field of Search ..................... 546/207; 71/94, 100

[56] References Cited

FOREIGN PATENT DOCUMENTS 2218097 11/1972 Fed. Rep. of Germany .
2168848 1/1972 France .
2324637 12/1976 France .

Primary Examiner—Catherine L. Mills
Attorney, Agent, or Firm—Felfe & Lynch

[57] ABSTRACT

N-Acyl-piperidone ketal compounds of the formula

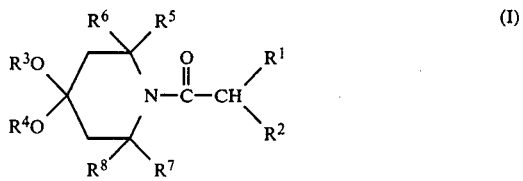

in which
$R^1$ represents alkyl or halogen,
$R^2$ represents halogen,
$R^3$ represents alkyl and
$R^4$ represents alkyl, or
$R^3$ and $R^4$ together represent an optionally branched alkylene chain, and
$R^5$, $R^6$, $R^7$ and $R^8$ independently of one another represent hydrogen or alkyl, and their use as antidotes for protecting crop plants from herbicidal damage.

9 Claims, No Drawings

N-ACYL-PIPERIDONE KETAL COMPOUNDS AND THEIR USE AS ANTIDOTES FOR PROTECTING CROP PLANTS FROM HERBICIDAL DAMAGE

This is a divisional application of Ser. No. 425,801 filed Sept. 28, 1982, now U.S. Pat. No. 4,548,639, which in turn is a continuation application of Ser. No. 166,280 filed July 7, 1980, abandoned.

This invention relates to certain new N-acyl-piperidone ketal compounds and to their use as antidotes for protecting crop plants from herbicidal damage, especially by herbicidally active thiolcarbamates and acetanilides. The invention further relates to new active compound combinations of the N-acyl-piperidone ketal compounds and certain herbicidally active carbamates and acetanilides which have particularly good selective herbicidal properties.

"Antidotes" ("safeners") in the present connection are to be understood as substances which are capable of specifically antagonising the harmful effects of herbicides on crop plants, that is to say of protecting the crop plants, without thereby noticeably influencing the herbicidal action on the weeds to be combated.

It is known that, when used for combating weeds in maize and other crops, certain thiolcarbamates and acetanilides cause damage to the crop plants to a greater or lesser extent. It is furthermore known that such compounds as, for example, N-dichloroacetyl-2-ethylpiperidine and N-dichloroacetyl-cis/trans-decahydroquinoline are suitable for reducing damage to crop plants by thiolcarbamates or acetanilides (see DE-OS (German Published Specification) No. 2,218,097). However, the activity of these substances as antidotes is not always completely satisfactory.

The present invention now provides, as new compounds, the N-acyl-piperidone ketals of the general formula

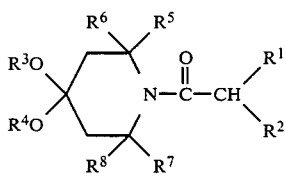

in which
  $R^1$ represents alkyl or halogen,
  $R^2$ represents halogen,
  $R^3$ represents alkyl and
  $R^4$ represents alkyl, or
  $R^3$ and $R^4$ together represent an optionally branched alkylene chain, and
  $R^5$, $R^6$, $R^7$ and $R^8$ independently of one another represent hydrogen or alkyl.

The invention also provides a process for the preparation of an N-acyl-piperidone ketal of the formula (I) in which
(a) a piperidone ketal of the general formula

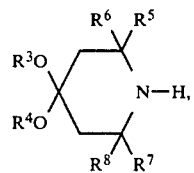

in which
  $R^3$, $R^4$, $R^5$, $R^6$, $R^7$ and $R^8$ have the meanings indicated above,
is reacted with an alkanoyl chloride of the general formula

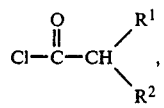

in which
  $R^1$ and $R^2$ have the meanings indicated above, if appropriate in the presence of a diluent and if appropriate in the presence of an acid-binding agent, or (b) an N-acyl-piperidone of the general formula

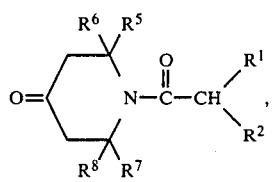

in which
  $R^1$, $R^2$, $R^5$, $R^6$, $R^7$ and $R^8$ have the meanings indicated above,
is reacted with an alcohol of the general formula

$$R^9\text{—OH} \qquad (V),$$

in which
  $R^9$ represents alkyl or ω-hydroxyalkyl,
in the presence of a catalyst or of a water-binding agent, and if appropriate in the presence of a diluent.

It has been found that N-acyl-piperidone ketals of the formula (I) are outstandingly suitable for protecting crop plants from damage by herbicidally active thiolcarbamates or by herbicidally active acetanilides.

It has also been found that the new active compound combinations comprising an N-acyl-piperidone ketal of the formula (I) and at least one herbicidally active thiolcarbamate and/or at least one herbicidally active acetanilide are outstandingly suitable for selectively combating weeds in crops of useful plants.

Surprisingly, herbicidal damage to crop plants by thiolcarbamates or by acetanilides is better suppressed when N-acyl-piperidone ketals of the formula (I) are also used than when the known compounds N-dichloroacetyl-2-ethyl-piperidine and N-dichloroacetyl-cis/trans-decahydroquinoline, which are chemically similar substances of the same type of action, are employed. Moreover, it was not to be expected that the active compound combinations according to the invention have better selective herbicidal properties than active compound combinations which consist of at least one herbicidally active thiolcarbamate or at least one herbicidally active acetanilide and N-dichloroacetyl-2-ethyl-piperidine, which is known as an antidote, or N-dichloroacetyl-cis/trans-decahydroquinoline, which is likewise known as an antidote.

The formula (I) provides a general definition of the N-acyl-piperidone ketals according to the invention. Preferably, in this formula, $R^1$ represents straight-chain or branched alkyl with 1 to 4 carbon atoms, chlorine or bromine, $R^2$ represents chlorine or bromine, $R^3$ represents straight-chain or branched alkyl with 1 to 4 carbon atoms, $R^4$ represents straight-chain or branched alkyl with 1 to 4 carbon atoms, or $R^3$ and $R^4$ together represent an alkylene chain which has 2 or 3 carbon atoms and is optionally substituted by methyl and/or ethyl, and $R^5$, $R^6$, $R^7$ and $R^8$ independently of one another represent hydrogen, methyl or ethyl.

If 4-glycolketal-piperidone and α-chloropropionic acid chloride are used as starting substances, the course of process variant (a) according to the invention can be represented by the following equation:

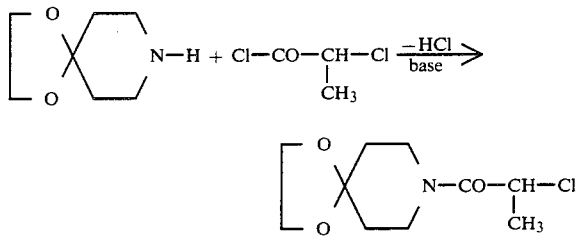

If N-dichloroacetyl-4-piperidone and methanol are used as starting substances, the course of process varient (b) according to the invention can be represented by the following equation:

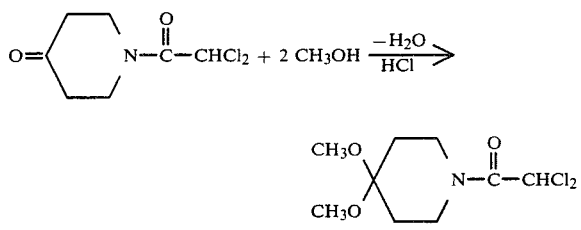

The formula (II) provides a general definition of the piperidone ketals required as starting substances in process variant (a). In this formula, $R^3$, $R^4$, $R^5$, $R^6$, $R^7$ and $R^8$ preferably have those meanings which have already been mentioned as preferred in connection with the description of the compounds of the formula (I).

Some of the piperidone ketals of the formula (II) are known (see Belgian Patent Specification No. 660,763 and Experientia 20, 437–438 (1964)). The piperidone ketals of the formula (II) which have not hitherto been described in the literature can be prepared in a simple manner by methods which are known in principle. Thus, piperidone ketals of the formula (II) are obtained when the corresponding 4-piperidones are reacted with the particular alcohols in the presence of an acid catalyst, for example hydrogen chloride, at temperatures between 0° C. and 50° C.

The formula (III) provides a general definition of the alkanoyl chlorides also required as starting substances in process variant (a). In this formula, $R^1$ and $R^2$ preferably have those meanings which have already been mentioned as preferred for $R^1$ and $R^2$ in connection with the description of the compounds of the formula (I).

The alkanoyl chlorides of the formula (III) are known, or they can be prepared in a simple manner by processes which are known in principle (see DE-OS (German Published Specification) No. 2,218,097).

Process variant (a) is preferably carried out in the presence of a diluent. Diluents which can be used in this process are water and inert organic solvents. These solvents include, as preferences, ketones, such as diethyl ketone and methyl isobutyl ketone; nitriles, such as propionitrile and acetonitrile; ethers, such as tetrahydrofuran or dioxan, aliphatic and aromatic hydrocarbons, such as petroleum ether, benzene, toluene and xylene; halogenated hydrocarbons, such as methylene chloride, carbon tetrachloride, chloroform or chlorobenzene; esters, such as ethyl acetate; and formamides, such as, in particular, dimethylformamide.

Possible acid-binding agents for carrying out process variant (a) are any of the customary acid acceptors. These include, as preferences, alkali metal hydroxides, such as sodium hydroxide and potassium hydroxide, alkali metal carbonates, such as sodium carbonate, potassium carbonate and sodium bicarbonate, and lower tertiary amines, such as triethylamine, dimethylbenzylamine, pyridine, diazabicyclooctane and 1,8-diaza-bicyclo[5.4.0]undec-7-ene. However, piperidone ketal of the formula (II) employed in excess can also simultaneously function as the acid-binding agent. In this case, it is not necessary to add an additional acid-binding agent.

The reaction temperatures can be varied within a substantial range in process variant (a). In general, the reaction is carried out between 0° and 100° C., preferably between 10° and 80° C.

In carrying out process variant (a), 1 to 2 moles of alkanoyl chloride of the formula (III) and, if appropriate, 1 mole of acid-binding agent are preferably employed per mole of piperidone ketal of the formula (II). Isolation of the reaction products is effected by customary methods. In general, a procedure is followed in which, when the reaction has ended, the reaction mixture is filtered, the filtrate is concentrated and, if appropriate, the residue which remains is recrystallized.

The formula (IV) provides a general definition of the N-acyl-piperidones required as starting substances in process variant (b). In this formula, $R^1$, $R^2$, $R^5$, $R^6$, $R^7$ and $R^8$ preferably have those meanings which have already been mentioned as preferred in connection with the description of the compounds of the formula (I).

The N-acyl-piperidones of the formula (IV) have not hitherto been described in the literature. However, they can be prepared in a simple manner by processes which are known in principle. Thus, N-acyl-piperidones of the formula (IV) are obtained when piperidones of the general formula

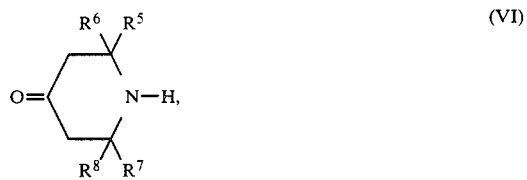

(VI)

in which $R^5$, $R^6$, $R^7$ and $R^8$ have the meanings indicated above, are reacted with alkanoyl chlorides of the general formula

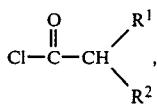 (III)

in which
$R^1$ and $R^2$ have the meanings indicated above, if appropriate in the presence of a diluent and if appropriate in the presence of an acid-binding agent.

Possible diluents and acid-binding agents are those solvents and acid acceptors which have already been mentioned in connection with process variant (a). The reaction temperatures and the other reaction conditions also correspond to those of process variant (a). The piperidones of the formula (VI) are known, or they can be prepared by processes which are known in principle.

The formula (V) provides a general definition of the alcohols also required as starting substances in process variant (b). In this formula, $R^9$ preferably represents straight-chain or branched alkyl with 1 to 4 carbon atoms or straight-chain or branched ω-hydroxyalkyl with 2 to 7 carbon atoms.

Specific examples of alcohols of the formula (V) which may be mentioned are: methanol, ethanol, propanol, ethylene glycol and propane-1,3-diol.

The alcohols of the formula (V) are known.

Catalysts which can be employed in carrying out process variant (b) are any of the compounds customarily used for ketalization reactions. These compounds include, as preferences, acids, such as hydrogen chloride, hydrogen bromide and toluenesulphonic acid.

The ketalization can also be carried out in the presence of a water-binding agent. Trimethylchlorosilane may be mentioned as an example.

Preferred diluents for carrying out process variant (b) are the alcohols functioning as reactants. However, it is also possible to employ other inert organic solvents. Preferred solvents in this case are aliphatic or aromatic, optionally halogenated hydrocarbons, for example benzene, toluene, methylene chloride, chloroform or carbon tetrachloride.

The reaction temperatures can be varied within a substantial range in carrying out process variant (b). In general, the reaction is carried out at temperatures between 0° C. and 200° C., preferably between 20° C. and 150° C.

In carrying out process variant (b), 2 to 3 moles or even a larger excess of alcohol of the formula (V) and a small amount of catalyst or an excess of water-binding agent are employed per mole of N-acyl-piperidone of the formula (IV). Isolation of the reaction products is effected by customary methods. In general, a procedure is followed in which the volatile components are carefully distilled off and, if appropriate, the residue is recrystallized.

As already mentioned, the N-acyl-piperidone ketals of the formula (I) are suitable for protecting crop plants from damage by herbicidally active thiolcarbamates and acetanilides without noticeably influencing their herbicidal action.

The N-acyl-piperidone ketals of the formula (I) can preferably be used as antidotes for protecting crop plants from damage by herbicidally active thiolcarbamates of the general formula

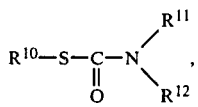 (VII)

in which
$R^{10}$ represents lower alkyl, benzyl, chlorobenzyl or alkoxybenzyl and
$R^{11}$ and $R^{12}$ independently of one another represent alkyl with 2 to 4 carbon atoms or cyclohexyl, or
$R^{11}$ and $R^{12}$, together with the adjacent nitrogen atom, represent a five-membered to seven-membered heterocyclic ring, and for protecting crop plants from damage by herbicidally active acetanilides of the general formula

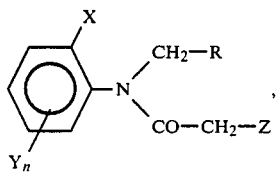 (VIII)

in which
R represents an optionally substituted N-containing heterocyclic radical,
X and Y are identical or different and represent alkyl,
Z represents halogen and
n represents 0, 1 or 2, and herbicidally active acid-addition salts and metal salt complexes thereof, and of the general formula

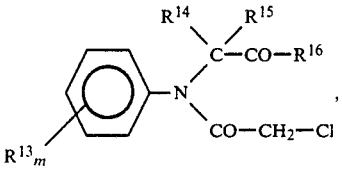 (IX)

in which
$R^{13}$ represents alkyl, halogen, haloaklyl, alkylthio, alkylsulphonyl, aminosulphonyl, cyano or nitro,
$R^{14}$ and $R^{15}$ are identical or different and represent hydrogen, alkyl, halogen, haloalkyl or optionally substituted phenyl,
$R^{16}$ represents alkyl or optionally substituted phenyl and
m represents 0 (zero) or an integer from 1 to 5, and of the general formula

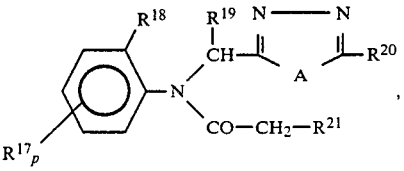 (X)

in which
A represents oxygen, sulphur or the grouping >$NR^{22}$,
$R^{19}$ represents hydrogen or alkyl, $R^{20}$ represents hydrogen, alkyl, haloalkyl, alkenyl, alkynyl, cycloalkyl, halogen, optionally substituted aryl, optionally substituted aralkyl or the grouping —$OR^{23}$, —$SR^{23}$ or —$NR^{22}R^{23}$, $R^{22}$ represents hydrogen, alkyl or optionally substituted aryl, $R^{23}$ represents hydrogen, alkyl, haloalkyl, alkenyl, alkynyl, cycloalkyl or optionally substituted aralkyl, $R^{17}$ represents alkyl, $R^{18}$ represents alkyl or halogen, $R^{21}$ represents halogen and p represents 0, 1 or 2, and of the formula

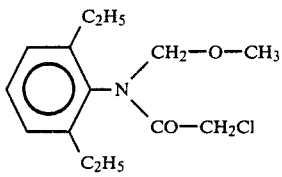 (XI)

and of the formula

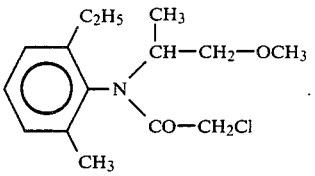 (XII)

Specific examples of thiolcarbamates of the formula (VII) which may be mentioned are: S-ethyl N,N-dipropylthiocarbamate, S-ethyl, N,N-diisobutylthiocarbamate, S-propyl N-butyl-N-ethylthiocarbamate, S-propyl N,N-diisopropylthiocarbamate, S-ethyl N,N-diethylthiocarbamate, S-ethyl N-ethyl-N-cyclohexylthiocarbamate, S-ethyl hexahydro-azepine-1-thiocarbamate, S-p-methoxybenzyl N,N-diethylthiocarbamate, S-p-chlorobenzyl N,N-diethylthiocarbamate, S-benzyl N,N-diethylthiocarbamate, S-benzyl N,N-di-sec.-butylthiocarbamate and S-propyl N-ethyl-N-butylthiocarbamate.

The thiolcarbamates of the formula (VII) and their herbicidal activity are already known (see U.S. Pat. Nos. 2,913,327, 3,037,853, 3,185,720, 3,198,786 and 3,582,314).

In the formula (VIII), R preferably represents an optionally substituted radical selected from pyrazol-1-yl, imidazol-1-yl, 1,2,4-triazol-1-yl, 1,2,3-triazol-1-yl, 1,3,4-triazol-1-yl, 1,2,3,4-tetrazol-1-yl and pyrrol-1-yl. Preferred substituents are: halogen (especially fluorine, chlorine and bromine) and alkyl with 1 to 4 carbon atoms. X and Y are identical or different and preferably represent straight-chain or branched alkyl with 1 to 4 carbon atoms. Z preferably represents chlorine or bromine and the index n represents 0, 1 or 2.

Specific examples of acetanilides of the formula (VIII) which may be mentioned are: 2-methyl-6-ethyl-N-(pyrazol-1-yl-methyl)-chloroacetanilide, 2,6-diethyl-N-(pyrazol-1-yl-methyl)-chloroacetanilide, 2,6-diethyl-N-(1,2,4-triazol-1-yl-methyl)-chloroacetanilide, 2,6-dimethyl-N-(1,2,4-triazol-1-yl-methyl)-chloroacetanilide, 2-methyl-N-(pyrazol-1-yl-methyl)-chloroacetanilide, 2,5-dimethyl-N-(pyrazol-1-yl-methyl)-chloroacetanilide, 2,3-dimethyl-N-(pyrazol-1-yl-methyl)-chloroacetanilide, 2-methyl-6-ethyl-N-(pyrazol-1-yl-methyl)-chloroacetanilide hydrochloride, 2,6-diethyl-N-(pyrazol-1-yl-methyl)-chloroacetanilide hydrochloride, 2,6-diethyl-N[(3,5-dimethylpyrazol-1-yl)-methyl]-chloroacetanilide, 2,6-diethyl-N-[(3-chloro-1,2,4-triazolyl)-methyl]-chloroacetanilide, 2-methyl-6-ethyl-N-[(3,5-dimethyl-pyrazol-1-yl)-methyl]-chloroacetanilide, 2-tert.-butyl-N-(pyrazol-1-yl-methyl)chloroacetanilide, 2-methyl-6-ethyl-N-[(3-bromo-5-methylpyrazol-1-yl)-methyl]-chloroacetanilide, 2-methyl-6-ethyl-N-[(3-chloro-1,2,4-triazolyl)-methyl]-chloroacetanilide and 2,6-diethyl-N-[(4-chloropyrazol-1-yl)-methyl]chloroacetanilide.

Further preferred acetanilides of the formula (VIII) are listed in the preparative examples.

The acetanilides of the formula (VIII) and their herbicidal activity, and herbicidally active acid addition salts and metal salt complexes thereof are already known (see DE-OS (German Published Specification) No. 2,648,008 and DE-OS (German Published Specification) No. 2,704,281).

In the formula (XI), $R^{13}$ preferably represents straight-chain or branched alkyl with 1 to 6 (especially 1 to 4) carbon atoms, halogen (especially fluorine, chlorine or bromine), haloalkyl with up to 3 carbon atoms and up to 5 identical or different halogen atoms (preferred halogens being fluorine or chlorine, and trifluoromethyl being mentioned as an example), alkylthio or alkylsulphonyl with in either case 1 to 4 carbon atoms in the alkyl part, aminosulphonyl, cyano or nitro. $R^{14}$ and $R^{15}$ are identical or different and preferably represent hydrogen, straight-chain or branched alkyl with 1 to 4 carbon atoms, halogen (especially fluorine, chlorine or bromine), haloalkyl with up to 3 carbon atoms and up to 5 identical or different halogen atoms (preferred halogens being fluorine and chlorine) or phenyl which is optionally mono-substituted or polysubstituted, preferred substituents being the radicals mentioned for $R^{13}$. $R^{16}$ preferably represents straight-chain or branched alkyl with 1 to 6 (especially 1 to 4) carbon atoms or phenyl which is optionally monosubstituted or polysubstituted, preferred substituents being: alkyl with 1 to 4 carbon atoms, halogen (especially fluorine, chlorine and bromine), haloalkyl with up to 3 carbon atoms and up to 5 identical or different halogen atoms (especially fluorine or chlorine atoms, trifluoromethyl being mentioned as an example), alkoxy, alkylthio or alkylsulphonyl with in each case 1 to 4 carbon atoms, aminosulphonyl, cyano, nitro or phenyl or phenoxy, in either case optionally substituted by chlorine. The index m preferably represents 1, 2 or 3.

Specific examples of acetanilides of the formula (IX) which may be mentioned are: 2,6-dimethyl-N-(benzoylmethyl)chloroacetanilide, 2,6-dimethyl-N-(4-chlorobenzoyl-methyl)chloroacetanilide and 2-methyl-6-ethyl-N-(benzoyl-methyl)chloroacetanilide.

Further preferred acetanilides of the formula (IX) are listed in the preparative examples.

The acetanilides of the formula (IX) and their herbicidal activity are already known (see DE-OS (German Published Specification) No. 2,726,253).

In the formula (X), A preferably represents oxygen, sulphur or the grouping —$NR^{22}$, wherein $R^{22}$ represents hydrogen, straight-chain or branched alkyl with 1 to 4 carbon atoms or aryl with 6 to 10 carbon atoms (especially phenyl), it being possible for the aryl radical to carry one or more substituents selected from halogen, alkyl with 1 to 4 carbon atoms, alkoxy with 1 or 2 carbon atoms, alkylthio with 1 or 2 carbon atoms, cyano, nitro and haloalkyl with up to 2 carbon atoms and up to 5 identical or different halogen atoms (preferred halogens being fluorine or chlorine). $R^{19}$ preferably represents hydrogen or methyl. $R^{20}$ in the formula (X) preferably represents hydrogen, straight-chain or branched alkyl with 1 to 4 carbon atoms, haloalkyl with up to 3 carbon atoms and up to 5 identical or different halogen atoms (preferred halogens being fluorine or chlorine, and trifluoromethyl being mentioned as an example), alkenyl or alkynyl with in either case 2 to 4 carbon atoms, cycloalkyl with 5 to 7 carbon atoms or halogen (especially fluorine, chlorine or bromine). $R^{20}$ furthermore preferably represents aryl with 6 to 10 carbon atoms (especially phenyl), it being possible for the aryl radical to carry one or more substituents selected from halogen, alkyl with 1 to 4 carbon atoms, alkoxy with 1 or 2 carbon atoms, alkylthio with 1 or 2 carbon atoms, cyano, nitro and haloalkyl with up to 2 carbon atoms and up to 5 identical or different halogen atoms (preferred halogens being fluorine or chlorine and trifluoromethyl being mentioned as a specific example of haloalkyl). $R^{20}$ furthermore preferably represents aralkyl with 6 to 10 carbon atoms in the aryl part and 1 to 4 carbon atoms in the alkyl part (especially benzyl), it being possible for the aralkyl radical to carry, on the aryl part, one or more substituents selected from halogen, alkyl with 1 to 4 carbon atoms, alkoxy with 1 or 2 carbon atoms, alkylthio with 1 to 2 carbon atoms, cyano, nitro and haloalkyl with up to 2 carbon atoms and up to 5 identical or different halogen atoms (preferred halogens being fluorine or chlorine, and trifluoromethyl being mentioned as a specific example of haloalkyl). $R^{20}$ also preferably represents the grouping $-OR^{23}$, $-SR^{23}$ or $-NR^{22}R^{23}$, wherein $R^{22}$ has the preferred meanings which have already been mentioned above for this radical, and $R^{23}$ represents hydrogen, straight-chain or branched alkyl with 1 to 4 carbon atoms, haloalkyl with 1 to 3 carbon atoms and up to 5 identical or different halogen atoms (preferred halogens being fluorine and chlorine, and trifluoromethyl being mentioned as an example), alkenyl or alkynyl with in either case 2 to 4 carbon atoms, cycloalkyl with 5 to 7 carbon atoms or aralkyl with 6 to 10 carbon atoms in the aryl part and 1 to 4 carbon atoms in the alkyl part (especially benzyl), it being possible for the aralkyl radical to carry, on the aryl part, one or more substituents selected from halogen, alkyl with 1 to 4 carbon atoms, alkoxy with 1 or 2 carbon atoms, alkylthio with 1 or 2 carbon atoms, cyano, nitro and haloalkyl with up to 2 carbon atoms and up to 5 identical or different halogen atoms (preferred halogen being fluorine or chlorine, and trifluoromethyl being mentioned as a specific example of haloalkyl). In the formula (X), $R^{17}$ preferably represents straight-chain or branched alkyl with 1 to 4 carbon atoms, $R^{18}$ preferably represents straight-chain or branched alkyl with 1 to 4 carbon atoms, fluorine, chlorine or bromine, and $R^{21}$ preferably represents chlorine, bromine or iodine. The index p represents 0, 1 or 2.

Specific examples of acetanilides of the formula (X) which may be mentioned are: 2,6-diethyl-N-[(2-methyl-1,3,4-oxadiazol-5-yl)-methyl]-chloroacetanilide, 2,6-dimethyl-N-[(2-methyl-1,3,4-oxadiazol-5-yl)-methyl]-chloroacetanilide, 2-ethyl-6-methyl-N-[(2-methyl-1,3,4-oxadiazol-5-yl)-methyl]-chloroacetanilide and 2-tert.-butyl-N-[(2-methyl-1,3,4-oxadiazol-5-yl)-methyl]-chloroacetanilide.

Further preferred acetanilides of the formula (X) are listed in the preparative examples.

The acetanilides of the formula (X) and their herbicidal activity have not hitherto been disclosed in the literature. They can be prepared in a simple manner. Thus, acetanilides of the the formula (X) are obtained by reacting n-azolylalkylanilines of the general formula

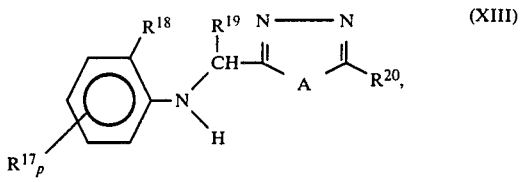

in which $R^{17}$, $R^{18}$, $R^{19}$, $R^{20}$, A and p have the meanings indicated above, with haloacetic acid chlorides or anhydrides of the general formula $$R^{21}-CH_2-CO-Cl \qquad (XIVa)$$

or $$(R^{21}-CH_2-CO)_2O \qquad (XIVb),$$

in which $R^{21}$ has the meaning indicated above, in the presence of a diluent and if appropriate in the presence of an acid-binding agent.

If 2,6-diethyl-N-(3-methylthio-4-methyl-1,2,4-triazol-5-yl-methyl)-aniline and chloroacetyl chloride are used as starting substances, the course of the reaction in the process for the preparation of the acetanilides of the formula (X) can be represented by the following equation:

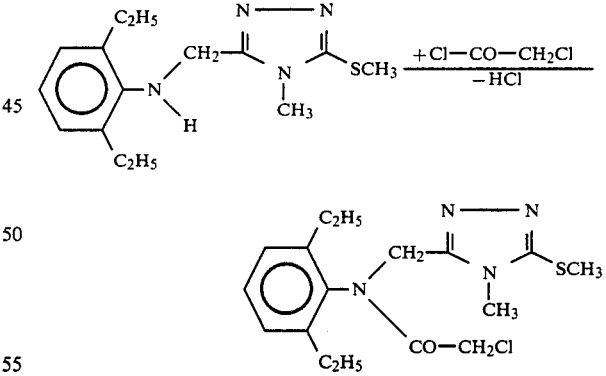

The formula (XIII) provides a general definition of the N-azolylalkylanilines required as starting substances in carrying out the process for the preparation of the acetanilides of the formula (X). In the formula (XIII), $R^{17}$, $R^{18}$, $R^{19}$, $R^{20}$, A and p preferably have those meanings which have already been mentioned as preferred in connection with the description of the acetanilides of the formula (X).

The N-azolylalkylanilides of the formula (XIII) required as starting substances in the process for the preparation of the acetanilides (X) have not hitherto been disclosed in the literature. However, they can be prepared in a simple manner by several processes. Thus, N-azolylalkylanilines of the formula (XIII) are obtained by (A) reacting anilines of the general formula

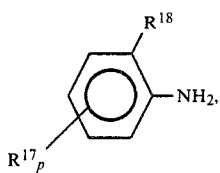 (XV)

in which
R$^{17}$, R$^{18}$ and p have the meanings indicated above, with azole derivatives of the general formula

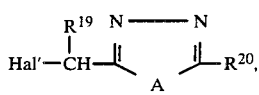 (XVI)

in which
A, R$^{19}$ and R$^{20}$ have the meanings indicated above and
Hal' represents chlorine or bromine,
in the presence of an acid-binding agent, for example potassium carbonate or sodium carbonate, and in the presence of an inert organic solvent, for example dimethylformamide or toluene, at temperatures betweeen 20° and 160° C., an excess of aniline of the formula (XV) preferably being employed (see also the preparative Examples), or (B) reacting hydrazine derivatives of the general formula

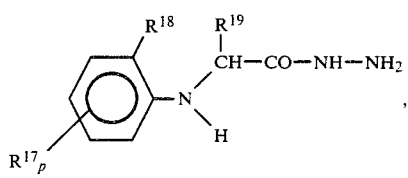 (XVII)

in which
R$^{17}$, R$^{18}$, R$^{19}$ and p have the meanings indicated above, with isocyanates or isothiocyanates of the general formula

   R$^{22}$—N=C=B   (XVIII), in which
B represents oxygen or sulphur and
R$^{22}$ has the meaning indicated above,
in the presence of an organic solvent, for example an alcohol, ether or hydrocarbon, at temperatures between 0° and 80° C., cyclizing the compounds formed, of the general formula

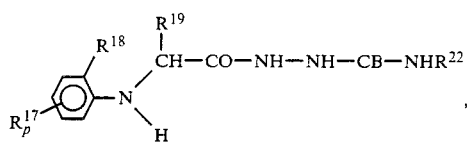 (XIX)

in which
B, R$^{17}$, R$^{18}$, R$^{19}$, R$^{22}$ and p have the meanings indicated above, at temperatures between 20° and 100° C. in the presence of a strong base, for example sodium hydroxide solution or potassium hydroxide solution, and in the presence of a solvent, for example ethanol or water, and reacting the triazolones or triazolethiones formed, of the general formula

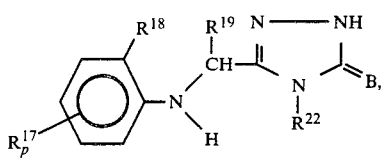 (XX)

in which
B, R$^{17}$, R$^{18}$, R$^{19}$, R$^{22}$ and p have the meanings indicated above,
with halides of the general formula

   Hal'—R$^{24}$   (XXI), in which
Hal' represents chlorine or bromine and
R$^{24}$ represents the radicals of the substituent R$^{23}$, with the exception of hydrogen,
in the presence of a strong base, for example sodium hydroxide solution, and in the presence of an inert organic solvent, for example toluene or methylene chloride, at temperatures between 20° and 80° C., it also being possible to carry out the reaction under phase transfer catalysis and using other alkylating reagents, for example dimethyl sulphate (see also the preparative Examples), or (C) reacting hydrazine derivatives of the general formula (XVII) with formic acid or acid chlorides or acid anhydrides of the general formula

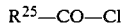   R$^{25}$—CO—Cl   (XXIIa)

or

   (R$^{25}$—CO—)$_2$O   (XXIIb), in which
R$^{25}$ represents alkyl, haloalkyl, alkenyl, alkynyl, cycloalkyl, optionally substituted aryl or optionally substituted aralkyl,
in the presence of an inert organic solvent, such as an ether, hydrocarbon or halogenated hydrocarbon, at temperatures between 0° and 50° C. and either cyclizing the compounds formed, of the general formula

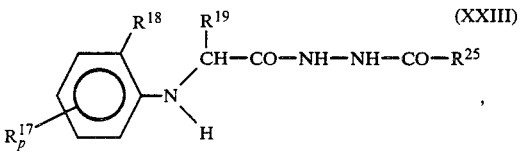 (XXIII)

in which
R$^{17}$, R$^{18}$, R$^{19}$, R$^{25}$ and p have the meanings indicated above,
with diphosphorus pentasulphide in a manner which is in itself known (see Chem. Ber. 32, 797 (1899) and J. prakt. Chemie 69, 145 (1904)) to give thiadiazole derivatives, or reacting them with customary dehydrating reagents, also in a known manner, to give oxadiazole derivatives (see, in this context, Elderfield, Heterocyclic Compounds, Volume 7 (1961)) or (D) reacting hydrazine derivatives of the general formula (XVII) with nitriles of the general formula

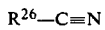 (XXIV), in which
R²⁶ represents alkyl, haloalkyl or optionally substituted aryl,
in a manner which is in itself known, to give triazole derivatives (see Chem. Ber. 96, 1064 (1963)), or (E) reacting hydrazine derivatives of the general formula (XVII) with imino-ethers of the general formula

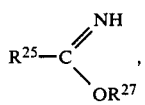 (XXV)

in which
R²⁵ represents alkyl, haloalkyl, alkenyl, alkynyl, cycloalkyl, optionally substituted aryl or optionally substituted aralkyl and
R²⁷ represents methyl or ethyl,
in a manner which is in itself known, under reflux and in the presence of an inert organic solvent, for example ethanol, to give oxadiazole derivatives, or (F) reacting the anilines of the formula (XV) with azolealdehydes of the general formula

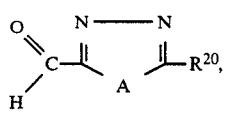 (XXVI)

in which
R²² has the meaning indicated above,
in the presence of an inert organic solvent, for example toluene, at temperatures between 80° and 120° C., and reducing the compounds formed, of the general formula

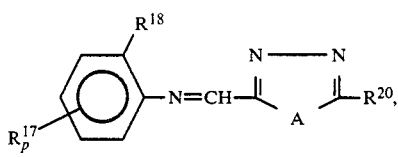 (XXVII)

in which
A, R¹⁷, R¹⁸, R²⁰ and p have the meanings indicated above,
in a generally known manner, for example by reaction with a complex hydride, such as sodium borohydride, if appropriate in the presence of a polar organic solvent, such as methanol, at temperatures between 0° and 80° C.

The compounds of the formulae (XV) and (XVI) required as starting substances in process (A) are known, or they can be prepared by processes which are known in principle (see Helv. Chim. Acta 55, 199 et seq. (1972), Chem. Ber. 32, 797 et seq. (1899) and Chem. Ber. 96, 1049 et seq. (1963)).

The starting substances of the formula (XVII) required in process (B) have not hitherto been disclosed in the literature. However, they can be prepared by known processes, by reacting known esters (see, inter alia, DT-OS's (German Published Specifications) Nos. 2,350,944 and 2,513,730) of the general formula

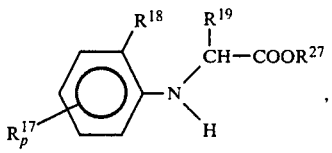 (XXVIII)

in which
R¹⁷, R¹⁸, R¹⁹ and p have the meanings indicated above and
R²⁷ represents methyl or ethyl,
with hydrazine hydrate, preferably in the presence of an organic solvent, for example ethanol, dioxan or dimethylformamide, at temperatures between 20° and 120° C. (see also the preparative Examples).

The reaction components of the formulae (XVIII) and (XXI) required in process (B) are generally known compounds of organic chemistry.

The substances of the formulae (XXIIa), (XXIIb), (XXIV) and (XXV) required as reaction components in processes (C), (D) and (E) are likewise known.

The azole-aldehydes of the formula (XXVI) to be used as reaction components in process (F) are also known, or they can be prepared by processes which are known in principle (see Elderfield, "Heterocyclic Compounds", Volume 7 (1961) and "Advances in Heterocyclic Chemistry", Volume 9 (1968)).

The formulae (XIVa) and (XIVb) provide general definitions of the haloacetic acid chlorides and anhydrides also required as starting substances in the preparation of the acetanilides of the formula (X). In the formulae (XIVa) and (XIVb), R²¹ preferably represents chlorine, bromine or iodine.

The haloacetic acid chlorides and anhydrides of the formulae (XIVa) and (XIVb) are generally known compounds of organic chemistry.

Preferred diluents for the reaction for the preparation of the acetanilides of the formula (X) are inert organic solvents. These include, as preferences, ketones, such as diethyl ketone, and in particular acetone and methyl ethyl ketone; nitriles, such as propionitrile, and in particular acetonitrile; ethers, such as tetrahydrofuran or dioxan; aliphatic and aromatic hydrocarbons, such as petroleum ether, benzene, toluene or xylene; halogenated hydrocarbons, such as methylene chloride, carbon tetrachloride, chloroform and chlorobenzene; and esters, such as ethyl acetate.

If appropriate, the process for the preparation of acetanilides of the formula (X) can be carried out in the presence of acid-binding agents (hydrogen chloride acceptors). Any of the customary acid-binding agents can be used in this process. These agents include, as preferences, organic bases, such as tertiary amines, for example triethylamine, or such as pyridine; and furthermore inorganic bases, for example alkali metal hydroxides and alkali metal carbonates.

The reaction temperatures can be varied within a substantial range in carrying out the process for the preparation of the acetanilides of the formula (X). In general, the reaction is carried out at temperatures between 0° C. and 120° C., preferably between 20° C. and 100° C.

1.5 moles of haloacetylating agent and 1 to 1.5 moles of acid-binding agent are generally employed in carrying out the process for the preparation of the acetanilides of the formula (X). Isolation of the compounds of the formula (X) is effected in the customary manner.

Further preferred acetanilides with which the compounds of the formula (I) according to the invention can be employed as antidotes are the compounds of the formulae (XI) and (XII). These substances and their herbicidal activity are already known (see U.S. Pat. No. 3,442,945 and DE-OS (German Published Specification) No. 2,328,340).

The N-acyl-piperidine ketals of the formula (I) according to the invention are particularly suitable for protecting important crop plants, such as maize, soya bean, cotton, sugar beet, cereals, rice and cane sugar, from herbicidal damage by thiolcarbamates and acetanilides.

The active compound combinations according to the invention, which comprise an N-acyl-piperidone ketal of the formula (I) and at least one herbicidally active thiolcarbamate and/or at least one herbicidally active acetanilide, exhibit a very good action against broad-leaved weeds and graminaceous weeds in numerous crops of useful plants. They can therefore be used for selectively combating weeds in numerous crops of useful plants. By weeds, in the broadest sense, there are to be understood in this context all plants which grow in locations where they are undesired.

The active compound combinations according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compound combinations according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

The active compound combinations according to the invention are particularly suitable for selectively combating weeds in maize, soya bean, cotton, sugar beet, cereals, rice and cane sugar.

The antidotes according to the invention can be converted, if appropriate as a mixture with the herbicidal active compounds with which they are employed, into the customary formulations, such as solutions, emulsions, wettable powders, suspensions, powders, dusting agents, foams, pastes, soluble powders, granules, suspension-emulsion concentrates, natural and synthetic materials impregnated with active compound, very fine capsules in polymeric substances and in coating compositions, for use on seed.

These formulations are produced in known manner, for example by mixing the antidotes according to the invention, if appropriate as a mixture with the herbicidal active compounds with which they are employed, with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain between 0.1 and 95% by weight of antidote or antidote and herbicidal active compound, preferably between 0.5 and 90%.

The antidotes according to the invention, as such or in the form of their formulations, can, as stated above, also be employed as mixtures with herbicidal active compounds, finished formulations or tank mixing being possible. Mixtures with other active compounds, such as fungicides, insecticides, acaricides, nematicides, bird repellants, growth factors, plant nutrients and agents which improve soil structure are also possible.

The antidotes according to the invention or mixtures of the antidotes according to the invention and a herbicidal active compound can be employed as such, in the form of their formulations or in the use forms prepared therefrom by further dilution, such as ready-to-use solutions, suspensions, emulsions, powders and granules. They may be used in the customary manner, for example by watering, spraying, atomizing, dusting or scattering, dry dressing, moist dressing, wet dressing, slurry dressing or encrusting.

The antidotes according to the invention can be applied by methods customary for antidotes of this type. Thus, the antidotes according to the invention can be applied either before or after the herbicide, or can be applied together with the herbicide. If the herbicide is used before or after sowing, crop plants can also be protected from damage by treating the seed with the antidotes before sowing (dressing). A further possible way of using the antidotes is to apply them to the seed furrow during sowing. If the plants are seedlings, these can be treated with the antidotes before being transplanted.

When the antidotes according to the invention are employed, the customary amounts, at the location, of the particular herbicides are applied. The amounts of herbicidal active compound used vary between 0.5 and 5 kg/ha. The amount of antidote used is independent of the herbicide and of the amount of herbicidal active compound used. In general, the amounts of antidotes according to the invention applied are between 0.1 and 5 kg/ha in the case of treatment of the soil surface, preferably between 0.2 and 4 kg/ha. In the case of seed treatment, the amounts of antidotes according to the invention applied are in general between 10 and 300 g per kilogram of seed, preferably between 25 and 200 g per kilogram of seed.

The weight ratios of antidotes to herbicidal active compounds in the active compound combinations according to the invention can vary within relatively wide limits. In general, 0.04 to 1.0 part by weight, preferably 0.1 to 0.5 part by weight, of antidote of the formula (I) is present per 1 part by weight of herbicidal active compound.

Thus, the present invention also provides an antidote composition containing as active ingredient a compound of the formula (I) in admixture with a solid diluent or carrier or in admixture with a liquid diluent or carrier containing a surface-active agent.

The present invention also provides a method of protecting crop plants from damage by herbicidally active thiolcarbamates or herbicidally active acetanilides, in which there is applied to the plants, or to a habitat thereof, a compound of the formula (I) alone or in the form of a composition containing as active ingredient a compound of the formula (I) in admixture with a diluent or carrier.

The present invention also provides crops protected from damage by herbicidally active thiolcarbamates or by herbicidally active acetanilides by being grown in areas in which immediately prior to and/or during the time of the growing a compound of the formula (I) was applied, alone or in admixture with a diluent or carrier.

The present invention also provides a herbicidal composition that contains as active ingredients (1) a compound of the formula (I) and (2) at least one herbicidally active compound selected from thiolcarbamates and acetanilides, alone or in admixture with a solid or liquid diluent or carrier.

The present invention also provides a method of combating weeds, in which there is applied to the weeds, or to a habitat thereof, a herbicidal composition according to the present invention.

The present invention further provides crops protected from damage by weeds by being grown in areas in which immediately prior to and/or during the time of the growing, a herbicidal composition of the present invention was applied.

It will be seen that the usual methods of providing a harvested crop may be improved by the present invention.

The good activity of the antidotes according to the invention can be seen from the example which follows.

In this example, the compounds indicated below are employed as comparison compounds:

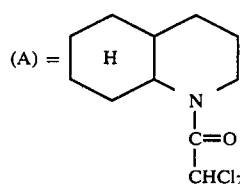

(N—Dichloroacetyl-cis/trans-decahydroquinoline)

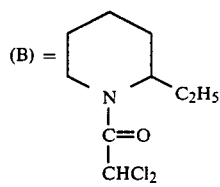

(N—Dichloroacetyl-2-ethyl-piperidine)

Furthermore, the acetanilide indicated below is employed as the herbicidal active compound in this example:

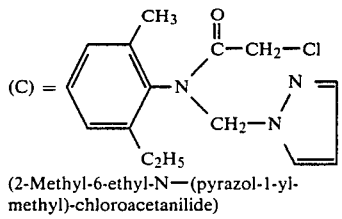

(2-Methyl-6-ethyl-N—(pyrazol-1-yl-methyl)-chloroacetanilide)

EXAMPLE A

Pre-emergence test

Solvent: 5 parts by weight of acetone
Emulsifier: 1 part by weight of alkylaryl polyglycol ether To produce a suitable preparation of active compound, 1 part by weight of herbicidal active compound or antidote, or of a mixture of antidote and herbicidal active compound, was mixed with the stated amount of solvent, the stated amount of emulsifier was added and the concentrate was diluted with water to the desired concentration.

Seeds of the test plants were sown in normal soil and, after 24 hours, watered with the herbicide preparation or antidote preparation or with the preparation of antidote and herbicidal active compound. It was expedient to keep constant the amount of water per unit area. The concentration of the active compound in the preparation was of no importance, only the amount of active compound applied per unit area being decisive. After three weeks, the degree of damage to the plants was rated in % damage in comparison to the development of the untreated control. The figures denoted:

0% = no action (like untreated control)
100% = total destruction

Evaluation of the test results showed that the compound (1) (see preparative Example 1) was more suitable for protecting crop plants from damage by the compound (C) than the comparison compounds (A) and (B).

PREPARATIVE EXAMPLES

Example 1

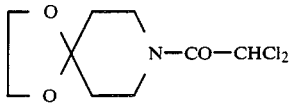 (1)

12.4 g (0.084 mol) of dichloroacetyl chloride was added dropwise to a mixture of 12 g (0.084 mol) of piperid-4-one ethylene ketal and 12.8 g (0.084 mol) of 1,8-diazobicyclo[5.4.0]undec-7-ene in 100 ml of toluene, whilst stirring, at a rate such that the temperature of the reaction mixture did not exceed 40° C. Thereafter, the mixture was subsequently stirred at 20° C. for 2 hours. Working up was then effected by a procedure in which the reaction mixture was filtered, the filtrate was concentrated under reduced pressure and the residue was recrystallized from a mixture of toluene and petroleum ether. 10.5 g (49% of theory) of N-dichloroacetylpiperid-4-one ethylene ketal were obtained in this manner in the form of colorless crystals of melting point 102° C.

Example 2

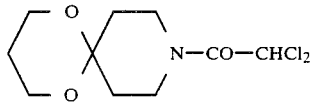 (2)

A mixture of 19 g (0.09 mol) of N-dichloroacetylpiperid-4-one, 7.5 g (0.099 mol) of propane-1,3-diol and 22.4 g (0.21 mol) of trimethylchlorosilane was boiled under reflux for 12 hours, while stirring. Thereafter, the reaction mixture was concentrated under reduced pressure and the residue was then subjected to brief incipient distillation under greatly reduced pressure. The resulting brown oil, which slowly crystallized completely, was recrystallized from 200 ml of toluene. 16 g (66.6% of theory) of N-dichloroacetyl-piperid-4-one propylene ketal of melting point 115° C. were obtained.

| Analysis: | C | H | Cl | N |
|---|---|---|---|---|
| calculated: | 44.7% | 5.5% | 26.4% | 5.2% |
| found: | 44.5% | 5.6% | 26.0% | 5.7% |

The N-acyl-piperidone ketals of the formula (I) listed in Table 1 below were also prepared by the methods analogous to those described in Examples 1 and 2.

TABLE 1

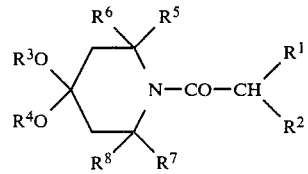 (I)

| Example No. | $R^1$ | $R^2$ | $R^3$ | $R^4$ | $R^5$ | $R^6$ | $R^7$ | $R^8$ | Refractive index or melting point [°C.] |
|---|---|---|---|---|---|---|---|---|---|
| 3 | Cl | Cl | $CH_3$ | $CH_3$ | H | H | H | H | 76 |
| 4 | Cl | Cl | $C_2H_5$ | $C_2H_5$ | H | H | H | H | 64 |
| 5 | $CH_3$ | Cl | —$CH_2$—$CH_2$— | | H | H | H | H | $n_D^{23}$ = 1.5059 |
| 6 | $CH_3$ | Cl | —$CH_2$—$CH_2$—$CH_2$— | | H | H | H | H | 70 |
| 7 | $CH_3$ | Cl | $C_2H_5$ | $C_2H_5$ | H | H | H | H | $n_D^{23}$ = 1.5091 |

Example (VIII-1)

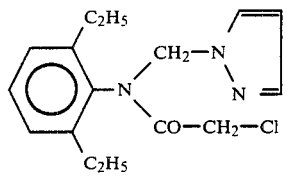

A mixture of 68 g (1 mol) of pyrazole and 106 g (1.05 mol) of triethylamine in 150 ml of anhydrous ethyl acetate was added to 274.2 g (1 mol) of 2,6-diethyl-N-chloromethyl-chloroacetanilide in 250 ml of anhydrous ethyl acetate, while stirring, whereupon the temperature rose to 30° C. The mixture was subsequently stirred at room temperature for 1 hour. There were two possibilities for the working up:

(1) The reaction mixture was filtered and the filtrate was washed with water until neutral, dried over sodium sulphate and evaporated in vacuo. After fractional crystallization of the residue with ligroin, 171.2 g (56% of theory) of 2,6-diethyl-N-(pyrazol-1-yl-methyl)-chloroacetanilide of melting point 67° C. were obtained in the form of colorless crystals.

(2) The reaction mixture was cooled to 0° C. and filtered and the residue on the filter was rinsed with 10 ml of cold ethyl acetate. 50 g (1.4 mol) of dry hydrogen chloride were passed into the filtrate at 0° to −10° C. The hydrochloride salts which had precipitated were then filtered off and rinsed with 50 ml of cold ethyl acetate and the solid residue was subsequently partitioned between 0.5 liter of ethyl acetate and 0.5 liter of aqueous sodium hydroxide solution with a pH value of 12. The organic phase was separated off, washed twice with 0.5 liter of sodium chloride solution each time, dried over sodium sulphate and evaporated in vacuo. 60 ml of benzine were added to the colorless oily residue, whereupon the residue crystallized. 220.2 g (72% of theory) of 2,6-diethyl-N-(pyrazol)-1-yl-methyl)-chloroacetanilide of melting point 67° C. were obtained in the form of colorless crystals.

The compounds listed in the table below are prepared in an analogous manner:

TABLE 2

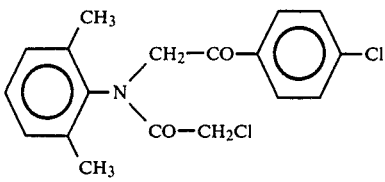

| Example No. | X | $Y_n$ | Z | R | Melting point (°C.) |
|---|---|---|---|---|---|
| VIII-2 | $C_2H_5$ | 6-$C_2H_5$ | Cl | 1,2,4-Triazol-1-yl | 112 |
| VIII-3 | i-$C_3H_7$ | 6-i-$C_3H_7$ | Cl | Pyrazol-1-yl | 134 |
| VIII-4 | $CH_3$ | 6-$C_2H_5$ | Cl | 1,2,4-Triazol-1-yl | 92 |
| VIII-5 | $CH_3$ | 6-$C_2H_5$ | Cl | Pyrazol-1-yl | 57 |
| VIII-6 | $C_2H_5$ | 4,6-$(CH_3)_2$ | Cl | Pyrazol-1-yl | 32 |
| VIII-7 | $CH_3$ | 4,6-$(CH_3)_2$ | Cl | Pyrazol-1-yl | 92 |
| VIII-8 | $C_2H_5$ | 4-$CH_3$, 6-$C_2H_5$ | Cl | Pyrazol-1-yl | 78 |
| VIII-9 | i-$C_3H_7$ | 6-i-$C_3H_7$ | Cl | 1,3,4-Triazol-1-yl | 196 |
| VIII-10 | i-$C_3H_7$ | 6-i-$C_3H_7$ | Cl | 1,2,4-Triazol-1-yl | 138 |
| VIII-11 | $C_2H_5$ | 6-$C_2H_5$ | Cl | Pyrrol-1-yl | oil |
| VIII-12 | i-$C_3H_7$ | — | Cl | 1,2,4-Triazol-1-yl | 118 |
| VIII-13 | $CH_3$ | 6-$C_2H_5$ | Cl | 1,2,3,4-Tetrazol-1-yl | oil |
| VIII-14 | i-$C_3H_7$ | — | Cl | Pyrazol-1-yl | oil |
| VIII-15 | $C_2H_5$ | — | Cl | 1,2,4-Triazol-1-yl | 81 |
| VIII-16 | $CH_3$ | 6-$CH_3$ | Cl | Pyrazol-1-yl | 82 |
| VIII-17 | $CH_3$ | 6-$CH_3$ | Cl | 1,2,4-Triazol-1-yl | 110 |
| VIII-18 | $CH_3$ | 5-$CH_3$ | Cl | 1,2,4-Triazol-1-yl | oil |
| VIII-19 | $CH_3$ | — | Cl | Pyrazol-1-yl | 56 |
| VIII-20 | $CH_3$ | — | Cl | 1,2,4-Triazol-1-yl | 88 |
| VIII-21 | $CH_3$ | 5-$CH_3$ | Cl | Pyrazol-1-yl | oil |
| VIII-22 | $CH_3$ | 3-$CH_3$ | Cl | 1,2,4-Triazol-1-yl | 114 |
| VIII-23 | $CH_3$ | 3-$CH_3$ | Cl | Pyrazol-1-yl | 102 |
| VIII-24 | $C_2H_5$ | 6-$CH_3$ | Cl | Pyrazol-1-yl (xHCl) | 87 |
| VIII-25 | $C_2H_5$ | 6-$C_2H_5$ | Cl | Pyrazol-1-yl (xHCl) | 67 |
| VIII-26 | $C_2H_5$ | 6-$C_2H_5$ | Cl | 3.5-Dimethyl-pyrazol-1-yl | 111 |
| VIII-27 | $C_2H_5$ | 6-$C_2H_5$ | Cl | Bromo-methyl-pyrazolyl | 145 |
| VIII-28 | $C_2H_5$ | 6-$C_2H_5$ | Cl | 3-Chloro-1,2,4-triazol-1-yl | 110 |
| VIII-29 | $CH_3$ | 6-$C_2H_5$ | Cl | 3,5-Dimethyl-pyrazol-1-yl | 90 |
| VIII-30 | $C_2H_5$ | 6-$C_2H_5$ | Cl | 3-Methyl-pyrazol-1-yl | 89 |
| VIII-31 | $C_2H_5$ | 6-$CH_3$ | Cl | 3-Methyl-pyrazol-1-yl | 113 |
| VIII-32 | $C(CH_3)_3$ | — | Cl | Pyrazol-1-yl | oil |
| VIII-33 | $C(CH_3)_3$ | — | Cl | 1,2,4-Triazol-1-yl | 118 |
| VIII-34 | $C_2H_5$ | 6-$CH_3$ | Cl | Bromo-methyl-pyrazolyl | 80 |
| VIII-35 | $CH_3$ | 6-$C_2H_5$ | Cl | 4-Chloro-pyrazol-1-yl | 91 |
| VIII-36 | $CH_3$ | 6-$C_2H_5$ | Cl | 3-Chloro-1,2,4-triazol-1-yl | 121 |
| VIII-37 | $C_2H_5$ | 6-$CH_3$ | Cl | 2,4,5-Trichloro-imidazol-1-yl | 158 |
| VIII-38 | $C_2H_5$ | 6-$C_2H_5$ | Cl | 4-Chloro-pyrazol-1-yl | 110 |
| VIII-39 | $C_2H_5$ | 6-$C_2H_5$ | Cl | 1,2,3,4-Tetrazol-1-yl | 110 |
| VIII-40 | $C_2H_5$ | 6-$C_2H_5$ | Br | Pyrazol-1-yl | 68 |
| VIII-41 | $CH_3$ | 6-$C_2H_5$ | Br | Pyrazol-1-yl | 67 |
| VIII-42 | $C_2H_5$ | 6-$C_2H_5$ | Cl | Imidazol-1-yl | oil |
| VIII-43 | $C_2H_5$ | 6-$C_2H_5$ | Br | 1,2,4-Triazol-1-yl | 90 |
| VIII-44 | $CH_3$ | 6-$C_2H_5$ | Br | 1,2,4-Triazol-1-yl | 78 |

Example (IX-1)

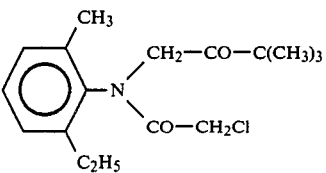

16 ml (0.2 mol) of chloroacetyl chloride were added dropwise to a solution of 18.5 g (0.068 mol) of 2,6-dimethyl-N-(4-chloro-benzylmethyl)-aniline in 150 ml of benzene. Thereafter, the mixture was stirred under reflux for 15 hours and was concentrated by distilling off the solvent and the excess chloroacetyl chloride in vacuo. The residue was triturated with a mixture of ether/petroleum ether (1:3) and the crystalline residue formed was filtered off and dried. 17.7 g (75.5% of theory) of 2,6-dimethyl-N-(4-chlorobenzyl-methyl)-chloroacetanilide of melting point 128° C. were obtained.

Example (IX-2)

23.3 g (0.1 mol) of 2-ethyl-6-methyl-N-pivaloyl-methylaniline were dissolved in 100 ml of benzene, and 24 ml (0.3 mol) of chloroacetyl chloride were added. Thereafter, the mixture was stirred under reflux for 15 hours and was concentrated by distilling off the solvent and the excess chloroacetyl chloride in vacuo. The oily residue was stirred with petroleum ether, the mixture was decanted the product phase was stirred with active charcoal and filtered and the filtrate was concentrated in vacuo. The residue was stirred with n-hexane and the resulting solid is filtered off and dried. 13.7 g (45% of theory) of 2-ethyl-6-methyl-N-pivaloylmethyl-chloroacetanilide of melting point 86° C. were obtained.

The compounds listed in Table 3 below were also prepared by the methods described in Examples (IX-1) and (IX-2).

The compounds listed thereafter in Table 4 below could also be obtained in an analogous manner.

TABLE 3

$$\text{(IX)}$$

Structure (IX): phenyl ring substituted with $R^{13}{}_m$ and bonded to N; N bonded to C($R^{14}$)($R^{15}$)–CO–$R^{16}$ and to CO–CH$_2$Cl.

| Example No. | $R^{13}{}_m$ | $R^{14}$ | $R^{15}$ | $R^{16}$ | Melting point (°C.) or refractive index |
|---|---|---|---|---|---|
| IX-3 | 2-CH$_3$ | H | H | phenyl | 138 |
| IX-4 | 2-CH$_3$ | H | H | 4-Cl-phenyl | 140 |
| IX-5 | 2,6-(C$_2$H$_5$)$_2$ | H | H | 4-Cl-phenyl | 134 |
| IX-6 | 2,6-(C$_2$H$_5$)$_2$ | H | H | phenyl | 116 |
| IX-7 | 2-Cl | H | H | 4-Cl-phenyl | 124 |
| IX-8 | 2,6-(CH$_3$)$_2$ | H | H | 4-CH$_3$-phenyl | 100 |
| IX-9 | 4-Cl | H | H | 2-Cl-phenyl | 114 |
| IX-10 | 2,6-(CH$_3$)$_2$ | CH$_3$ | H | CH$_3$ | 104 |
| IX-11 | 2,6-(i-C$_3$H$_7$)$_2$ | H | H | 2-Cl-phenyl | 200 |
| IX-12 | 2,6-(X$_2$H$_5$)$_2$, 4-CH$_3$ | H | H | phenyl | 112 |
| IX-13 | 2,6-(i-C$_3$H$_7$)$_2$ | H | H | 4-CH$_3$-phenyl | 140 |
| IX-14 | 2,6-(CH$_3$)$_2$ | H | H | 3,4-(CH$_3$)$_2$-phenyl | 90 |

TABLE 3-continued $$(IX)$$

Structure: Phenyl ring with $R^{13}_m$ substituent, N attached to ring, N bonded to $CO-CH_2Cl$ and to $C(R^{14})(R^{15})-CO-R^{16}$

| Example No. | $R^{13}_m$ | $R^{14}$ | $R^{15}$ | $R^{16}$ | Melting point (°C.) or refractive index |
|---|---|---|---|---|---|
| IX-15 | 2-$C_2H_5$, 6-$CH_3$ | H | H | 4-Cl-phenyl | 70 |
| IX-16 | 2,6-$(CH_2)_2$ | H | H | 2,3-dimethoxyphenyl | 114 |
| IX-17 | 2-$C_2H_5$, 4,6-$(CH_3)_2$ | H | H | phenyl | $n_D^{20} = 1.5680$ |
| IX-18 | 2,6-$(CH_3)_2$ | H | H | 4-F-phenyl | 104 |
| IX-19 | 2,4,6-$(CH_3)_3$ | H | H | 4-Cl-phenyl | 134 |
| IX-20 | 2,4,6-$(CH_3)_3$ | H | H | phenyl | $n_D^{20} = 1.5610$ |
| IX-21 | 2,6-$(CH_3)_2$ | H | phenyl | 4-Cl-phenyl | 149 |
| IX-22 | 2,6-$(CH_3)_2$ | H | $CH_3$ | phenyl | 84 |

TABLE 4

$$(IX)$$

| Example No. | $R^{13}_m$ | $R^{14}$ | $R^{15}$ | $R^{16}$ |
|---|---|---|---|---|
| IX-23 | 3,5-$(CF_3)_2$ | H | H | 4-Cl-phenyl |

TABLE 4-continued $$\text{(IX)} \quad R^{13}{}_m\text{-}C_6H_4\text{-}N(CO\text{-}CH_2Cl)\text{-}C(R^{14})(R^{15})\text{-}CO\text{-}R^{16}$$

| Example No. | $R^{13}{}_m$ | $R^{14}$ | $R^{15}$ | $R^{16}$ |
|---|---|---|---|---|
| IX-24 | 2,6-(CH$_3$)$_2$ | H | H | 4-NO$_2$-C$_6$H$_4$- |
| IX-25 | 2,6-(CH$_3$)$_2$ | H | H | 4-CN-C$_6$H$_4$- |
| IX-26 | 2,6-(CH$_3$)$_2$ | H | H | 4-C(CH$_3$)$_3$-C$_6$H$_4$- |
| IX-27 | 2,6-(CH$_3$)$_2$, 4-SO$_2$NH$_2$ | H | H | 4-Cl-C$_6$H$_4$- |
| IX-28 | 2-Cl, 6-CH$_3$ | H | H | 4-Cl-C$_6$H$_4$- |
| IX-29 | 2-C$_2$H$_5$, 6-CH$_3$ | CH$_3$ | CH$_3$ | C$_6$H$_5$- |
| IX-30 | 2-C$_2$H$_5$, 6-CH$_3$ | CH$_3$ | CH$_3$ | 4-C$_6$H$_5$-C$_6$H$_4$- |
| IX-31 | 2-C$_2$H$_5$, 6-CH$_3$ | CH$_3$ | CH$_3$ | 4-C$_6$H$_5$O-C$_6$H$_4$- |
| IX-32 | 2-C$_2$H$_5$, 6-CH$_3$ | CH$_3$ | CH$_3$ | 4-(4-Cl-C$_6$H$_4$)-C$_6$H$_4$- |
| IX-33 | 2-C$_2$H$_5$, 6-CH$_3$ | CH$_3$ | CH$_3$ | 4-Cl-C$_6$H$_4$- |
| IX-34 | 2-C$_2$H$_5$, 6-CH$_3$ | H | CH$_3$ | 4-Cl-C$_6$H$_4$- |
| IX-35 | 2-C$_2$H$_5$, 6-CH$_3$ | H | CH$_3$ | 4-(4-Cl-C$_6$H$_4$)-C$_6$H$_4$- |

TABLE 4-continued (IX)

Structure: R¹³ₘ-phenyl-N(CO-CH₂Cl)-C(R¹⁴)(R¹⁵)-CO-R¹⁶

| Example No. | $R^{13}_m$ | $R^{14}$ | $R^{15}$ | $R^{16}$ |
|---|---|---|---|---|
| IX-36 | 2,6-(CH₃)₂ | H | –C₆H₄–Cl | –C₆H₄–Cl |
| IX-37 | 2,6-(CH₃)₂ | H | –C₆H₄–F | –C₆H₄–Cl |
| IX-38 | 2,6-(CH₃)₂ | H | –C₆H₄–CH₃ | –C₆H₅ |
| IX-39 | 2,6-(CH₃)₂ | H | –C₆H₅ | –C₆H₅ |
| IX-40 | 2,6-(CH₃)₂ | H | –C₆H₄–Cl | –C₆H₅ |
| IX-41 | 2,6-(CH₃)₂ | H | CH₃ | –C₆H₄–Cl |

Example (X-1)

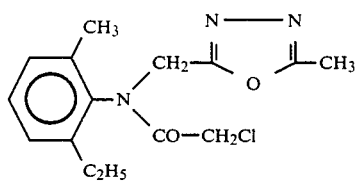

16.3 g (0.07 mol) of 2-ethyl-6-methyl-N-[(2-methyl-1,3,4-oxadiazol-6-yl)-methyl]-aniline and 6 g (0.076 mol) of anhydrous pyridine in 100 ml of absolute tetrahydrofuran were heated to the boiling point, while stirring, and a solution of 8 g (0.07 mol) of chloroacetyl chloride in 20 ml of tetrahydrofuran was added dropwise. When the dropwise addition had ended, the mixture was subsequently stirred for 10 minutes and was concentrated by distilling off the solvent and the residue was stirred with 150 ml of water. The reaction product which crystallized out was filtered off, washed with water and dried. 18.7 g (87% of theory) of beige-colored crystals of 2-ethyl-6-methyl-N-[(2-methyl-1,3,4-oxadiazol-5-yl)-methyl]-chloroacetanilide of melting point 67° to 70° C. were obtained.

Preparation of the starting material

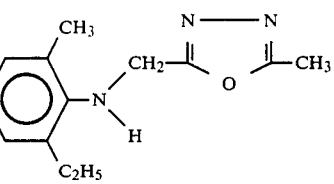

A mixture of 101.2 g (0.76 mol) of 2-ethyl-6-methylaniline, 40 g (0.3 mol) of 2-methyl-5-chloromethyl-1,3,5-oxadiazole, 41.4 g (0.3 mol) of powdered potassium carbonate and 76 ml of dimethylformamide was heated to 100° C. under reflux for 5 hours. Thereafter, the reaction mixture was filtered and the filtrate was diluted with methylene chloride and washed several times with water. The methylene chloride phase was dried over sodium sulphate and concentrated by distilling off the solvent in vacuo. The residue was distilled in vacuo. 46.8 g (67.5% of theory) of a yellowish oil consisting of 2-ethyl-6-methyl-N-[(2-methyl-1,3,4-oxadiazol-5-yl)-methyl]-aniline with a boiling point of 140° to 142° C./0.1 mm and a purity of 94% (determined by gas chromatography) were obtained.

Example (X-2)

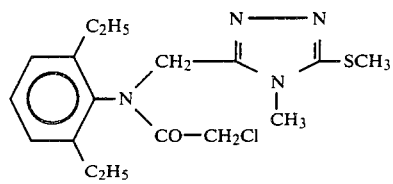

5 g (0.017 mol) of 2,6-diethyl-N-[(1-methyl-2-methylthio-1,3,4-triazol-5-yl)-methyl]-aniline and 1.6 g (0.02 mol) of pyridine were stirred in 100 ml of absolute tetrahydrofuran, and 2.3 g (0.02 mol) of chloroacetyl chloride were added dropwise at room temperature, whereupon the temperature rose to about 30° C. The mixture was stirred for 2 hours and was partly concentrated by distilling off the solvent, and water was added. The product which crystallized out was filtered off, dried and recrystallized from diisopropyl ether/ethyl acetate. 5 g (80% of theory) of 2,6-diethyl-N-[(1-methyl-2-methylthio-1,3,4-triazol-5-yl)-methyl]-chloroacetanilide of melting point 121° to 123° C. were obtained.

Preparation of the precursors

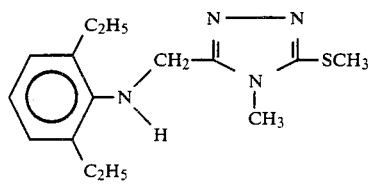

13.9 g (0.05 mol) of 2,6-diethyl-N-[(1-methyl-2-thiono-1,3,4-triazol-5-yl)-methyl]-aniline were stirred rapidly, at room temperature, in a two-phase mixture of 150 ml of toluene and 40 ml of 50% strength sodium hydroxide solution, with the addition of 1.5 g of triethyl-benzyl-ammonium chloride (TEBA) as a catalyst, and 6.3 g (0.05 mol) of dimethyl sulphate were added dropwise, whereupon the temperature rose to about 25° C. The mixture was subsequently stirred for 5 hours and the toluene phase was separated off, washed several times with water, dried over sodium sulphate and concentrated by distilling off the solvent. The oil which remained was made to crystallize by adding petroleum ether. After recrystallization from petroleum ether, 6.7 g (40% of theory) of 2,6-diethyl-N-[(1-methyl-2-methylthio-1,3,4-triazol-5-yl)-methyl]-aniline of melting point 65° to 67° C. were obtained.

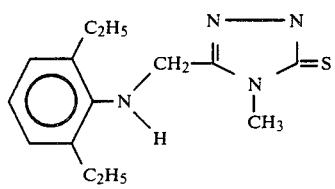

29.6 g (0.1 mol) of 1-methyl-4-[(2,6-diethylanilino)-acetyl]-thiosemicarbazide were suspended in 150 ml of ethanol and, after adding 7 g of potassium hydroxide in 20 ml of water, the mixture was heated under reflux for 1 hour. Thereafter, most of the solvent was distilled off and 250 ml of water were added to the residue. After acidifying the mixture to pH 5 with glacial acetic acid, the precipitate formed was filtered off and washed thoroughly with water. After drying, 27 g (97% of theory) of 2,6-diethyl-N-[(1-methyl-2-thiono-1,3,4-triazol-5-yl)-methyl]-aniline of melting point 117° to 121° C. were obtained.

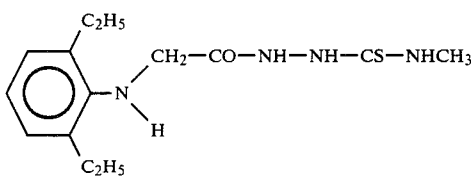

44.2 g (0.2 mol) of 2,6-diethyl-anilino-acetic acid hydrazide and 14.8 g (0.2 mol) of methyl isothiocyanate were dissolved in 250 ml of ethanol and the solution was heated to the reflux temperature for one hour. After subsequently cooling the solution to room temperature, the precipitate which had formed was filtered off and rinsed twice with 50 ml of ethanol each time. After drying, 46 g (78% of theory) of 1-methyl-4-[(2,6-diethyl-anilino)-acetyl]-thiosemicarbazide were obtained in the form of a colourless crystalline substance of melting point 166° C.

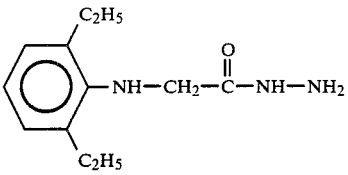

58.7 g (0.25 mol) of 2,6-diethyl-anilino-acetic acid ethyl ester and 25 g of hydrazine hydrate were left to stand in 200 ml of ethanol for 24 hours. Thereafter the mixture was concentrated by distilling off the solvent and the residue was extracted by stirring with water. After drying the product, 50.5 g (91% of theory) of colourless crystals of 2,6-diethyl-anilino-acetic acid hydrazide of melting point 71° to 73° C. were obtained.

Those compounds listed by means of their formulae in Table 5 were obtained in a corresponding manner.

TABLE 5

(X)

| Example No. | $R^{19}$ | $R^{20}$ | $R^{18}$ | $R^{17}_p$ | A | $R^{21}$ | Melting point (°C.) |
|---|---|---|---|---|---|---|---|
| X-3 | H | $CH_3$ | $C_2H_5$ | 6-$C_2H_5$ | O | Cl | 79–82 |
| X-4 | H | $CH_3$ | $CH_3$ | 6-$CH_3$ | O | Cl | 91–93 |
| X-5 | H | $CH_3$ | $C(CH_3)_3$ | — | O | Cl | 102–04 |
| X-6 | H | —S—$CH_2$—CH=$CH_2$ | $C_2H_5$ | 6-$C_2H_5$ | 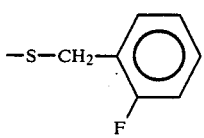 | Cl | 67–70° C. |
| X-7 | H |  | $CH_3$ | 6-$C_3H_5$ | 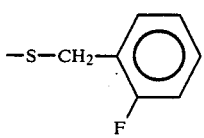 | Cl | 115–20 |
| X-8 | H | $C_2H_5$ | $CH_3$ | 6-$C_2H_5$ | O | Cl | 57–59 |
| X-9 | H | $C_2H_5$ | $C_2H_5$ | 6-$C_2H_5$ | O | Cl | 43–47 |
| X-10 | H | i-$C_3H_7$ | $CH_3$ | 6-$C_2H_5$ | O | Cl | viscous oil |
| X-11 | H | $CH_3$ | $CH_3$ | 3-$CH_3$ | 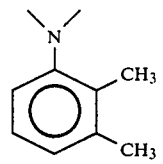 | Cl | glass-like solid |
| X-12 | H | $CH_3$ | $C_2H_5$ | 6-$C_2H_5$ | O | Br | 80° |
| X-13 | H | $CH_3$ | $CH_3$ | 6-$C_2H_5$ | O | Br | 92–94° C. |
| X-14 | H | $CH_3$ | i-$C_3H_7$ | 6-i-$C_3H_7$ | O | Cl | 135–37° |

The starting materials listed by means of their formulae in Table 6 below were obtained by one or more of the processes described in the present specification.

TABLE 6

(XIII)

| Example No. | $R^{19}$ | $R^{20}$ | $R^{18}$ | $R^{17}_p$ | A | Melting point (°C.) or refractive index |
|---|---|---|---|---|---|---|
| XIII-1 | H | $CH_3$ | $C_2H_5$ | 6-$C_2H_5$ | O | $n_D^{22} = 1.540$ |
| XIII-2 | H | $CH_3$ | $CH_3$ | 6-$C_2H_5$ | O | $n_D^{22} = 1.347$ |
| XIII-3 | H | $CH_3$ | $CH_3$ | 6-$CH_3$ | O | $n_D^{22} = 1.552$ |
| XIII-4 | H | $CH_3$ | —$(CH_3)_3$ | — | O | 52–55 |
| XIII-5 | H | $CH_3$ | i-$C_3H_7$ | 6-i-$C_3H_7$ | O | 96–99 |
| XIII-6 | H | $C_2H_5$ | $C_2H_5$ | 6-$C_2H_5$ | O | $n_D^{22} = 1.534$ |
| XIII-7 | H | $C_2H_5$ | $CH_3$ | 6-$C_2H_5$ | O | $n_D^{21} = 1.342$ |
| XIII-8 | H | i-$C_3H_7$ | $CH_3$ | 6-$C_2H_5$ | O | $n_D^{21} = 1.531$ |
| XIII-9 | H | $SCH_3$ | $C_2H_5$ | 6-$C_2H_5$ |  | 65–67 |
| XIII-10 | H | S—$CH_2$—CH=$CH_2$ | $C_2H_5$ | 6-$C_2H_5$ |  | $n_D^{21} = 1.577$ |

TABLE 6-continued

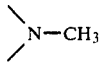

| Example No. | R$^{19}$ | R$^{20}$ | R$^{18}$ | R$^{17}{}_p$ | A | Melting point (°C.) or refractive index |
|---|---|---|---|---|---|---|
| XIII-11 | H | F (S—CH$_2$—phenyl) | CH$_3$ | 6-C$_2$H$_5$ | \N—CH$_3$/ | viscous oil |
| XIII-12 | H | CH$_3$ | CH$_3$ | 3-CH$_3$ | \N—(phenyl with CH$_3$, CH$_3$)/ | 142–143 |

It will be understood that the specification and examples are illustrative, but not limitative of the present invention and that other embodiments within the spirit and scope of the invention will suggest themselves to those skilled in the art.

What is claimed is:

1. N-acyl-piperidone ketal compound of the formula

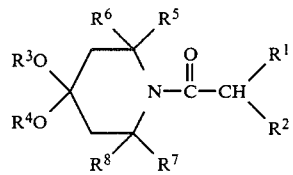

wherein
R$^1$ is alkyl with from 1 to 4 carbon atoms or chlorine;
R$^2$ is chlorine;

R$^3$ and R$^4$ together represent an alkylene chain of 2 to 3 carbon atoms; and
R$^5$, R$^6$, R$^7$ and R$^8$ are hydrogen.

2. Compound as claimed in claim 1 wherein R$^1$ is chlorine.

3. Compounds as claimed in claim 1 wherein R$^1$ is bromine or chlorine.

4. N-acyl-piperidone ketal compound as claimed in claim 1 designated N-dichloroacetyl-piperid-4-one ethylene ketal.

5. N-acyl-piperidone ketal compound as claimed in claim 1 designated N-dichloroacetyl-piperid-4-one propylene ketal.

6. N-acyl-piperidone ketal compound as claimed in claim 1 designated N-α-chloropropionyl-piperid-4-one ethylene ketal.

7. N-acyl-piperidone ketal compound as claimed in claim 1 designated N-α-chloropropionyl-piperid-4-one propylene ketal.

8. An antidote composition for protecting crop plants from herbicidal damage comprising as an active ingredient an antidotal amount of at least one N-acyl-piperidone ketal compound as claimed in claim 1.

9. An antidote composition as claimed in claim 8 containing from 0.1 to 95% of the said compound by weight.

* * * * *